(12) United States Patent
Cui et al.

(10) Patent No.: US 6,194,016 B1
(45) Date of Patent: Feb. 27, 2001

(54) EXTRACTION PROCESS AND USE OF YELLOW MUSTARD GUM

(76) Inventors: Wuwei (Steve) Cui, 6458 Western Skies Way, Mississauga, ON (CA), L5W 1H5; N. A. Michael Eskin, 1544 Mathers Bay West, Winnipeg, Manitoba (CA), R3T 2N2; Nam Fong Han, 21 Cimarron Cres, Nepean, ON. (CA), K2G 6E1; Zhi Zhong Duan, 1499 Meadowbrook Rd., Gloucester, Ont. (CA), K1B 5J9; Xiao Ying Zhang, 2415 Southvale Cres. Unit 105, Ottawa, Ont. (CA), K1B 4V1

(*) Notice: Subject to any disclaimer, the term of this patent is extended or adjusted under 35 U.S.C. 154(b) by 0 days.

(21) Appl. No.: 09/561,504

(22) Filed: Apr. 28, 2000

(30) Foreign Application Priority Data

Apr. 30, 1999 (CA) .................................................. 2270750

(51) Int. Cl.[7] ........................... C08B 37/00; C08B 15/00; C08B 29/00
(52) U.S. Cl. ........................ 426/463; 426/430; 426/431; 426/506; 426/511; 426/419
(58) Field of Search .................................. 426/425, 430, 426/431, 506, 511, 629, 655, 463, 419, 443, 567; 508/142, 216; 523/128

(56) References Cited

U.S. PATENT DOCUMENTS 3,878,195 * 4/1975 Taillie et al. .......................... 260/212
4,980,186   12/1990 Sharafabadi .

OTHER PUBLICATIONS

Cui, W., Eskin, N.A.M. and Biliaderis, C.G. (1993a). Chemical and physical properties of yellow mustard (*Sinapis alba* L.) mucilage. Food Chem., 46, 169–176.

Cui, W., Eskin, N.A.M. and biliaderis, C.G. (1993b). Water–soluble yellow mustard (*Sniapis alba* L.) polysaccharides: partial characterization, molecular size distribution and rheological properties. Carbohydr. Polm., 20, 215–225.

Cui, W., Eskin, N.A.M. and Biliaderis, C.G. (1994a). Fractionation, structural analysis and rheological properties of water–soluble yellow mustard (*Sinapis alba* L.) polysacchrides. J. Agric. Food Chem.42, 657–664.

Cui, W., Eskin, N.A.M. and Billiaderis, C.G. (1994b). Yellow mustard mucilage: chemical structure and rheological properties. Food Hydrocoll., 8, 204–213.

Cui, W., Mazza, G., Oomah, B.D.,and Biliaderis, C.G. (1994c). Optimization of an aqueous extraction process of flaxseed gum by response surface methodology. Lebenms. Wiss. u.–Technol. 8, 363–369.

Cui, W., Eskin, N.A.M. and Biliaderis, C.G. (1995a). NMR characterization of a 1,4–linked βD–glucan having ether groups from yellow mustard (*Sinapis alba* L.) mucilage. Carbohydr. Polym., 27 , 117–122.

Cui, W., Eskin, N.A.M., Biliaderis, C.G. and Mazza, G. (1995b). Synergistic intertactions between polysaccharides and galactomannans. Carbohydr. Polym., 27, 123–127.

Cui, W., Eskin, N.A.M., Biliaderis, C.G. and Marat, K. (1995c). NMR characterization of a 4–O–Methyl–β–D–glucuronic acid containing rhamnogalacturonan from yellow mustard (*Sinapis alba* L.) mucilage. Carbohydr. Res., 292.

Cui, W. and Eskin, N.A.M. Yellow mustard gum: I. Optimization of extraction process and rheological properties.

Gacula, M.C. and Singh, J. (1984). Statistical methods in food and consumer research. Academic Press. pp. 241.

Giovanni, M., (1983) response surface methodology and product optimization. Food. Technol., 11, 41–45.

Henika, R. G. (1982). Use of response surface methodology in sensory evaluation. Food Technol. 36(11), 96–101.

Lui, Hua and Eskin, N. A. Michael (1997). Interactions of native and acetylated pea starch with yellow mustard mucilage, locust and bean gum gelatin. Food Hydrocolloids, 12.

Philips, Glyn O., Williams, P.A. and Wedlock, David J. (1996). Gums and stabilisers for the food industry 8. Tokyo: IRL Press.

Siddiqui, I.R., Yiu, J.D., Jones, J.D. and Kalab, M. (1986). Mucilage in yellow mustard (*Brassica hirta*) seeds. Food Microstruct., 5, 157–162.

Tong, P.S., Jordan, W. K. and Houghton, G. (1984). Response surface methodology to study fat destabilization and development of overrun in ice cream produced with polyunsaturated safflower oil and milk fat blends. J. Dairy Sci., 67, 779–793.

Haaland, P.D. (1989). Experimental Design in Biotechnology. Marcel Dekker, Inc., New York and Basel. p. 243.

* cited by examiner

*Primary Examiner*—Jon P. Weber
*Assistant Examiner*—Patricia D Patten
(74) *Attorney, Agent, or Firm*—Kohn & Associates (57) ABSTRACT

The present invention provides for optimal extraction conditions for extracting yellow mustard gum from yellow mustard bran to provide for high yield. The four variables examined were extraction temperature, pH, water:solid ratio and extraction time. Of these variables, temperature and pH had a much greater influence on the yield and rheological properties of the extracted gum compared to water/solid ratio and extraction time. Optimum extraction conditions were temperatures between 50–70° C., pH 7–10, water/solid ratio of 40:1–60:1 and extraction time of 2–2.5 hr. The yield of gum obtained under the optimum extraction conditions was 30% of bran weight. The extracted gum exhibited maximum shear thinning flow behaviours. It can be incorporated into cosmetic products and skin lotions.

7 Claims, 8 Drawing Sheets

EXTRACTION PROCESS AND USE OF YELLOW MUSTARD GUM

CROSS-REFERENCE TO RELATED APPLICATIONS

This application claims priority on Canadian Serial No. 2,270,750, filed Apr. 30, 1999, and which is incorporated herein by reference.

FIELD OF THE INVENTION

The present invention relates to the field of yellow mustard gum, and in particular, its uses, and optimum processes for extraction of the gum from yellow mustard bran.

BACKGROUND OF THE INVENTION

Yellow mustard is one of the major crops in Western Canada. Commercially, yellow mustard seeds are processed into condiments and other food ingredients (Sharafabadi, 1990) while the bran by-product has little commercial value. The brans are rich in water-soluble mucilaginous material deposited on the outer layer of the testa (Sidiqui et al., 1986). Yellow mustard mucilage is composed of water-soluble polysaccharides containing two major fractions: a cellulose-like neutral polysaccharide fraction and a pectic-like acidic polysaccharide fraction (Cui et al., 1993b, 1994a, 1995a,b).

Earlier publications revealed that yellow mustard mucilage extracted from whole seed exhibited unique rheological properties in aqueous systems and excellent emulsion capacity and stability in oil/water systems (Cui et al., 1993a, 1994b). These properties are desirable for making yellow mustard mucilage commercially viable as a hydrocolloid gum for food and non-food applications. Preliminary studies indicated that 30–40% of the bran could be extracted as gum although the rheological properties of the extracted gum varied with extraction conditions.

The extracted yellow mustard gum exhibited rheological properties giving it the ability to interact with galactomannans synergistically (Cui, et al., 1995c).

U.S. Pat. No. 4,980,186 issued to Sharafabadi discloses a process for extracting yellow mustard gum. The process is a water extraction and is time-temperature dependent. The patent teaches that the resulting gum composition depends to some extent on the extraction process. The particular process used to extract the gum may change some of the rheological properties of the gum and therefore influence its suitability for use in certain products.

Sharafabadi teaches that the whole seed is treated with water in a first step and then the water extract is separated from the seed. The yellow mustard gum is contained in the water extract and may be precipitated using a number of well known methods. Sharafabadi teaches a broad temperature range for extraction in the range of 55–100° C. and a water:seed ratio which must be in the range of 2:1–7:1 for the 17 hour extraction in order for the extraction to be effective. Sharafabadi obtains approximately 4% yield of gum after 4–5 multiple extractions extending over approximately 17 hours (as compared to 5.3% yield reported by Cui 1993a which represents an incomplete extraction of mucilage from whole mustard seeds). This extraction has the disadvantage of requiring large amounts of water to satisfy the water:seed ratio. As well, this large amount of water is boiled during the extraction process and therefore is a very energy demanding process to obtain a small yield of mucilage. As well, due to the extended extraction time necessary for this process, Sharafabadi added a small amount of chloroform to prevent microbial fermentation. Chloroform is a known carcinogen and it is not desirable to use it in any product for internal or external use by individuals.

It is therefore desirable to provide for a process to extract yellow mustard gum over a shorter time period and more economically. It is also desirable to provide for an improved extraction process resulting in a high yield of yellow mustard gum having unique rheological properties.

It is also desirable to provide for yellow mustard gum which is able to interact with galactomannans improving the viscosity and gel structure for use in products applicable to skin.

SUMMARY OF THE INVENTION

The present invention therefore provides an optimal extraction process to produce yellow mustard gum (YMG) high in both yield and quality. The extraction process occurs over a shorter period of time than in the prior art.

The present invention further provides a use for the yellow mustard gum in products applicable to skin. It may be used in cosmetic and skin care formulations and produces a gel-like structure.

There therefore is provided a process for extracting the gum from yellow mustard bran, including a first step of treating the mustard bran with water to form a water:solid solution, a second step of separating the resulting water extract from the seed bran, and a third step of separating the yellow mustard gum from the water, wherein in the first step, the water is at a temperature in the range of about 50–70° C. and the water:solid ratio is in the range of about 40:1–60:1; in the second step, the pH of the water:solid solution is in the range of about 7.0–10.0; and the extraction time of the process is in the range of about 2 to 2.5 hours.

A further aspect of the present invention also provides a yellow mustard gum produced by this process.

A further aspect of the present invention provides for a composition suitable for application to the skin including yellow mustard gum produced according to the process outlined above.

BRIEF DESCRIPTION OF THE FIGURES

Preferred embodiments may now be described and may be better understood when read in conjunction with the Figures in which.

DETAILED DESCRIPTION OF THE INVENTION

The present invention provides for an improved extraction process for extracting yellow mustard gum from the bran only rather than from the whole seed. A standard water extraction process was used to extract the yellow mustard gum. The optimization experiments were carried out according to a central composite design with 4 factors and 5 levels (Haaland, 1989). A standard extraction process involves soaking the yellow mustard bran in water, heating the solution, and altering the pH to provide for optimum extraction of the gum. The water is then separated from the bran and the gum is precipitated from it.

The resulting yellow mustard gum extracted from the bran as described herein has a composition which differs from that produced when extracted from the whole seed. Gum extracted from whole seed as described in the Sharafabadi patent is comprised of approximately 42% glucose, 32% galactose, 10% mannose, 6% arabinose, 3% rhamnose, and 3% xylose. In contrast, the yellow mustard gum of the present invention contains about half as much of each of these sugars except for rhamnose. Rhamnose is present at 3–4 times the level reported in the Sharafabadi patent. It also contains over 18% uronic acid and 12% β-glucan neither of which was reported as being present by Sharafabadi.

Response Surface Methodology (RSM) was used for the optimization process. Four independent variables including temperature ($X_1$), pH ($X_2$), water/solid ratio ($X_3$) and time ($X_4$) were examined based on preliminary tests. Two dependent responses, yield and apparent viscosity of the gum solution/dispersion, were determined to evaluate the optimization process of extracting the yellow mustard gum from the brans. The rheological properties of YMG extracted under the optimum conditions were examined for its shear thinning flow behaviour and its ability to interact with galactomannans synergistically (Cui et al., 1995c).

The optimization experiments were carried out according to a central composite design with 4 factors and 5 levels (Haaland, 1989). The end and central values were chosen from the results of preliminary tests. As presented in Table 1, the coded values of the independent variables are arranged as −1.68 (lowest level), −1, 0 (medium level), +1 and +1.68 (highest level) which have the same predictive power in all directions from the centre point with the best precision (Gacula and Singh, 1984). Yield and apparent viscosity of the extracted materials were the dependent variables correspondents used to evaluate the products. The complete design consisted of 28 experimental points including 4 replications of the centre point and the experiment was carried out in a random order.

TABLE 1

Process variables and experimental data (coded and uncoded values) for the four-factor, five-level response surface design of yellow mustard gum aqueous extraction process

| Run Order Ratio | T (° C.) | pH (mPa · s) | Solid/ Water | Time (Hr) | Yield (%) | Viscosity |
|---|---|---|---|---|---|---|
| 1 | −1(40) | −1(4.0) | −1(25) | −1(2) | 15.5 | 7.09 |
| 2 | −1(40) | −1(4.0) | −1(25) | +1(4) | 17.2 | 10.44 |
| 3 | −1(40) | −1(4.0) | +1(55) | −1(2) | 15.8 | 6.07 |
| 4 | −1(40) | −1(4.0) | +1(55) | +1(4) | 18.9 | 17.87 |
| 5 | −1(40) | +1(8.0) | −1(25) | −1(2) | 24.6 | 26.57 |
| 6 | −1(40) | +1(8.0) | −1(25) | +1(4) | 24.9 | 28.87 |
| 7 | −1(40) | +1(8.0) | +1(55) | −1(2) | 26.7 | 30.40 |
| 8 | −1(40) | +1(8.0) | +1(55) | +1(4) | 30.0 | 27.44 |
| 9 | +1(80) | −1(4.0) | −1(25) | −1(2) | 20.3 | 17.92 |
| 10 | +1(80) | −1(4.0) | −1(25) | +1(4) | 23.8 | 12.66 |
| 11 | +1(80) | −1(4.0) | +1(55) | −1(2) | 19.1 | 7.18 |
| 12 | +1(80) | −1(4.0) | +1(55) | +1(4) | 22.5 | 7.97 |
| 13 | +1(80) | +1(8.0) | −1(25) | −1(2) | 25.1 | 29.20 |
| 14 | +1(80) | +1(8.0) | +1(55) | +1(4) | 25.5 | 26.28 |
| 15 | +1(80) | +1(8.0) | −1(25) | −1(2) | 27.3 | 29.43 |
| 16 | +1(80) | +1(8.0) | +1(55) | +1(4) | 27.7 | 22.71 |
| 17 | −2(20) | 0(6.0) | 0(40) | 0(3) | 19.2 | 10.81 |
| 18 | +2(100) | 0(6.0) | 0(40) | 0(3) | 23.7 | 7.95 |
| 19 | 0(60) | −2(2.0) | 0(40) | 0(3) | 29.4 | 6.22 |
| 20 | 0(60) | +2(10.0) | 0(40) | 0(3) | 39.0 | 20.68 |
| 21 | 0(60) | 0(6.0) | −2(10)* | 0(3) | 21.1 | 11.44 |
| 22 | 0(60) | 0(6.0) | +2(70) | 0(3) | 26.2 | 23.28 |
| 23 | 0(60) | 0(6.0) | 0(40) | −2(1) | 21.7 | 21.49 |
| 24 | 0(60) | 0(6.0) | 0(40) | +2(5) | 25.5 | 25.38 |
| 25 | 0(60) | 0(6.0) | 0(40) | 0(3) | 24.8 | 26.92 |
| 26 | 0(60) | 0(6.0) | 0(40) | 0(3) | 22.1 | 26.19 |
| 27 | 0(60) | 0(6.0) | 0(40) | 0(3) | 23.1 | 27.14 |
| 28 | 0(60) | 0(6.0) | 0(40) | 0(3) | 22.4 | 21.84 |

*Design value was 10, however, due to difficulty of operation, actual value of 18 was used for both experiment and the statistic analysis.

Measurements of Yield and Apparent Viscosity:

Yellow mustard gum (YMG) was extracted from commercial brans under conditions described by the centre composite experiment design (Haaland, 1989), as specified in Table 1. At the end of the extraction, pH of the slurry was adjusted to pH 6 using 1M NaOH and/or 1M HCl before centrifugation at 3000 g for 10 min (25° C.). The supernatant was separated from the residue then freeze-dried. The yield was calculated based on the weight of the freeze-dried material and the weight of the brans used (5.00 gram). The apparent viscosity of 1.0% of the extracted gum solution/dispersion was determined on a Bohlin VOR Rheometer using the C-25 system (Bohlin Reologi, Sweden) at 25° C., shear rate 93.32 $s^{-1}$.

Yield and apparent viscosity of yellow mustard gum (YMG) are the two important criteria for evaluating extraction efficiency. The apparent viscosity of YMG is not only related to its purity, but also reflects the type of polysaccharides extracted, as water-soluble polysaccharides are the only components contributing to the rheological properties. Previous studies revealed that YMG is composed of neutral and acidic polysaccharide fractions which exhibited different rheological properties (Cui et al., 1995a,b)

Figure 1:
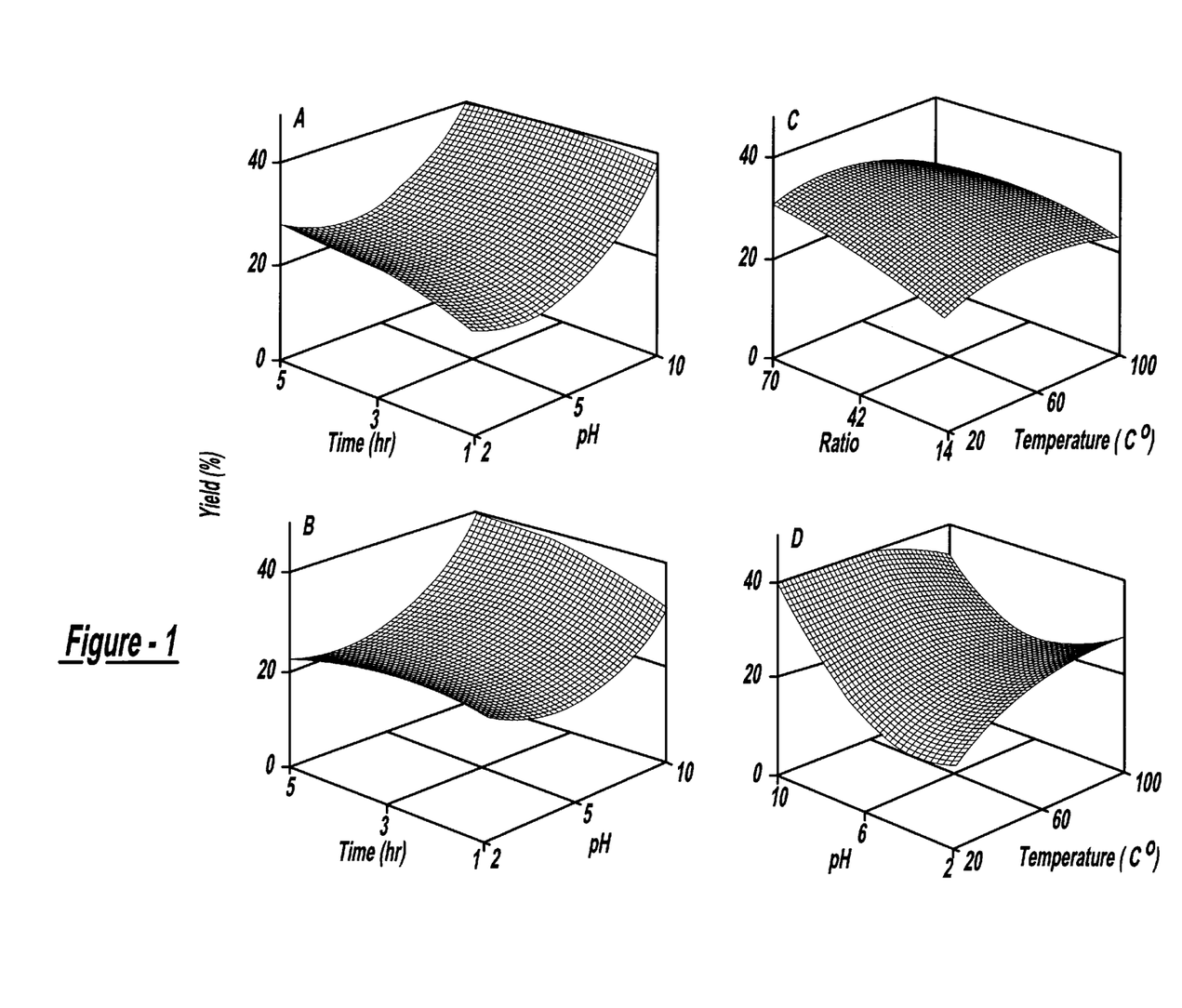
FIG. 1 illustrates the effect of extraction conditions on the yield of YMG where A is Time and pH (Temperature=60° C., Ratio=50) ; B is Ratio and pH (Temperature=60° C., Time=3hr); C is Ratio and Temperature (pH=8.5, Time=3hr) and D is pH and Temperature (Ratio=50, Time=3hr).
Figure 2:
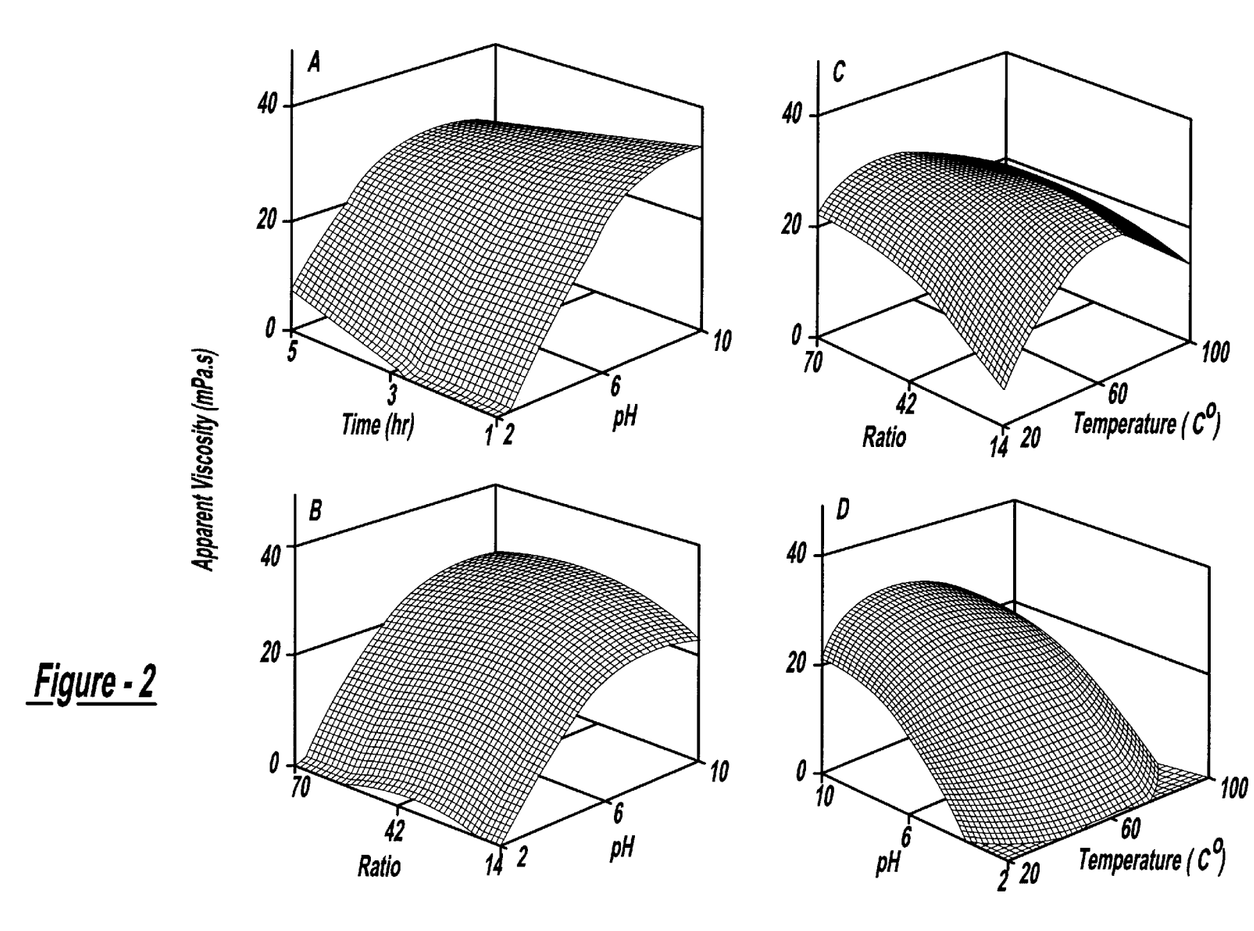
FIG. 2 illustrates the effect of extraction conditions on the apparent viscosity of YMG where A is Time and pH (Temperature=60° C., Ratio=50); B is Ratio and pH (Temperature=60° C., Time=3hr); C is Ratio and Temperature (pH=8.5, Time=3hr) and D is pH and Temperature (Ratio=50, Time=3hr).

The effect of temperature, pH, water/solid ratio and extraction time on the yield and apparent viscosity of YMG is presented in FIGS. 1 and 2, respectively. As shown in FIG. 1, the yield of YMG changed substantially with temperature and pH, while the water/solid ratio and time only had a slight effect. At a constant water/solid ratio (50/1) and extraction time (3 h), higher yields are obtained at higher pH regions. The lowest yield is observed at a lower pH zone (FIG. 1a). At pH 8.5 with an extraction time of 3 h, the highest yield was observed in the middle of the temperature range examined (~60° C.) (FIG. 1b). At the central region of temperature, the yield increased with the increase in water/solid ratio; the rate of the increase however, was faster at lower levels of water/solid ratio than at higher levels (FIG. 1b). A plot of yield against water/solid ratio and pH showed no significant changes along the water/solid ratio axis. In contrast, the yield changed substantially with changes in pH, as shown in FIG. 1c. The highest yield could be obtained at high pH region (8–10), while the lowest yield was observed over the pH range 4–6. The yield increased slightly as the pH further decreased, which may be due to the solubilization of proteins. The effect of extraction time on the yield is shown in FIG. 1d. YMG yield generally increased with extraction time, however, it appeared that time only had a slight effect on yield after two hours.

The strong effects of pH and temperature on the yield of YMG are supported by their regression coefficients which are highly significant ($\beta_1$ significant at 0.01 level; $\beta_2$ significant at 0.1 level; $\beta_{11}$ significant at 0.1 level; $\beta_{22}$ significant at 0.01 level). In contrast, the effects of water/solid ratio and extraction time on yield were not significant. The only significant interactions was observed between temperature and pH, which was significant at 0.05 level.

The effect of the four parameters, i.e. temperature, pH, water/solid ratio and time, on the apparent viscosity of YMG is shown in FIG. 2. In the plot of apparent viscosity against pH and temperature (water/solid ratio and time were fixed at 50:1 and 3 h, respectively), an optimum region was observed between pH 7–10 and temperature 45–65° C. In the plot of apparent viscosity against water/solid ratio and temperature, the highest apparent viscosity was observed at a temperature of 60° C. which was much less affected by the water/solid ratio. At lower temperatures (20–40° C.), the viscosity increased steadily with an increase in water/solid ratio. When extraction temperature and time are constants, the apparent viscosity increased steadily with an increase in pH and almost unaffected by the water/solid ratio. A maximum apparent viscosity plateau was achieved at high pH (8–10) and a water/solid ratio of about 55:1 (FIG. 2c). As shown in FIG. 2d, there was a slight effect of time on apparent viscosity although there appeared to be a general trend in which apparent viscosity decreased with the increase in extraction time.

The significant influence of temperature and pH on apparent viscosity are supported by their regression coefficients where $\beta_1$ and $\beta_{11}$ were significant at 0.01 level and $\beta_2$ and $\beta_{22}$ significant at 0.05 and 0.1 levels, respectively. No significant interactions were observed among the four factors examined on apparent viscosity (Table 2).

Figure 3:
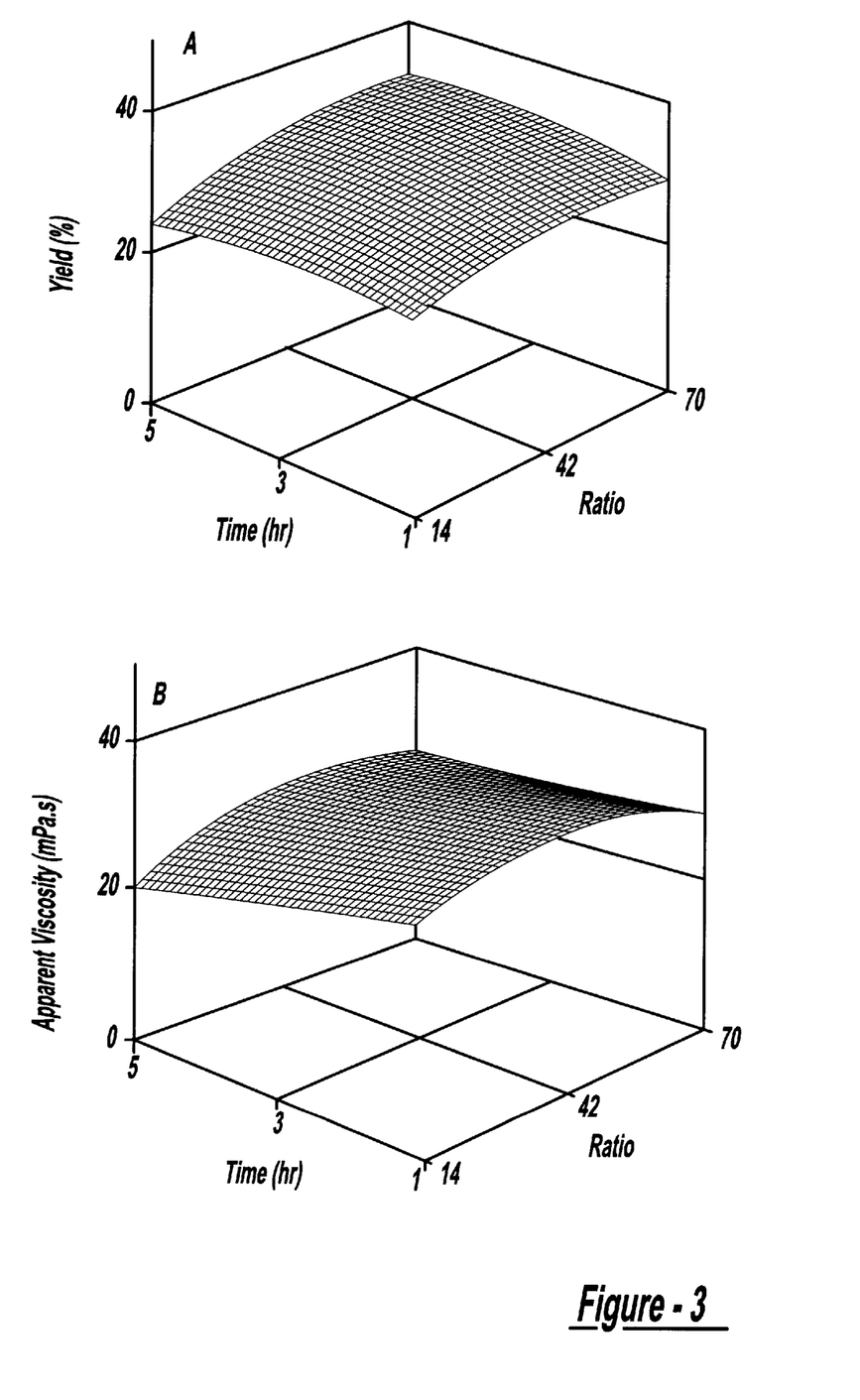
FIG. 3 illustrates the effect of extraction time and liquid/solid ratio on yield (A) and apparent viscosity (B) of YMG.
Figure 4:
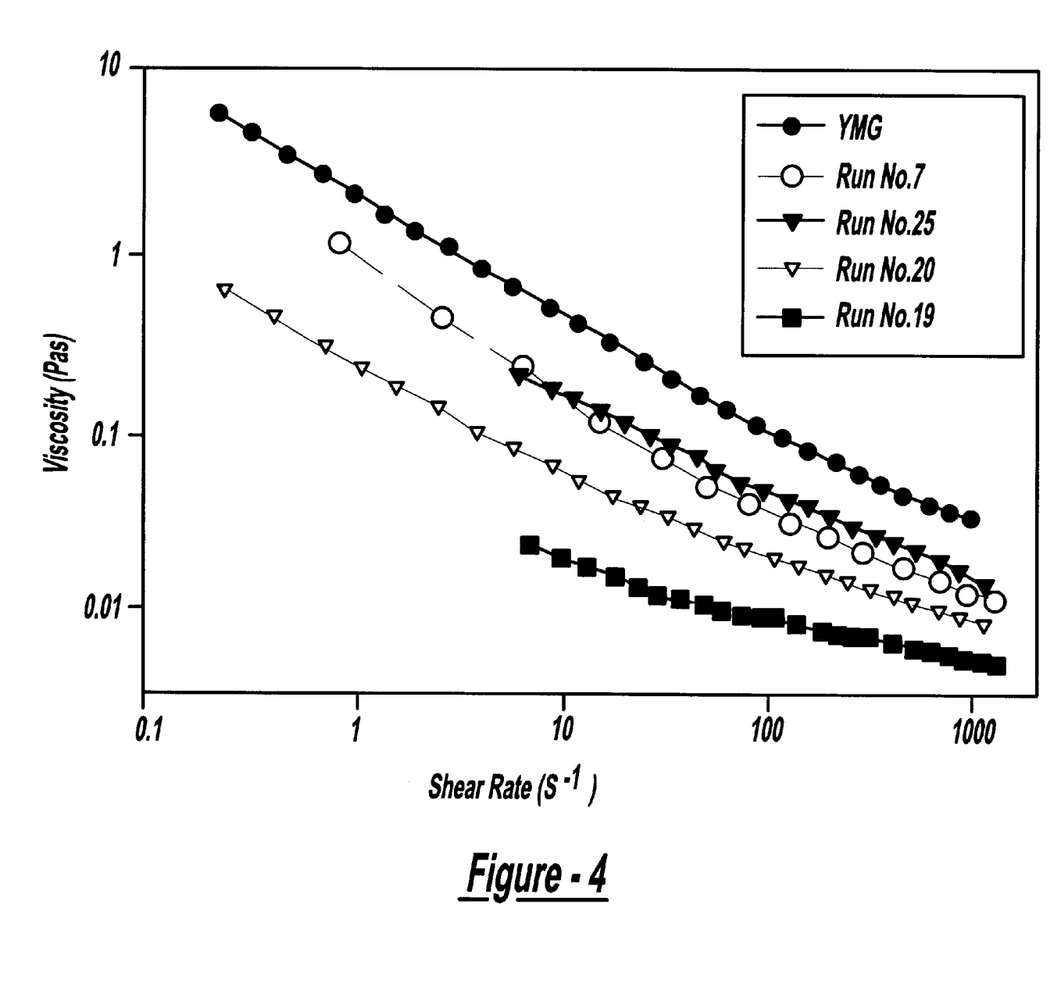
FIG. 4 illustrates the comparison of steady state viscosity vs shear rate of YMG and gums extracted from varied conditions (Table 1). Polymer concentration was 2.0% (23° C.).

The insignificant effect of water/solid ratio and extraction time on both yield and apparent viscosity of YMG are more obvious when these two dependents were plotted against these two factors at constant temperature and pH (FIG. 3). The effect of water/solid ratio was greater than that of time, as the yield increased with the ratio with an optimum observed for the apparent viscosity at about 60. Nevertheless, the effect of ratio and time on the extraction was much smaller compared to pH and temperature (FIG. 1 and 2).

By summarizing the optimization process, optimum extraction conditions were identified at temperatures of 50–70° C. with a preferred temperature of 55° C., pH of 7.0–10.0 with a preferred range of 8.0–9.5, water:solid ratio of 40:1–60:1 with a preferred ratio of 50:1 and extract-on time of 2–2.5 hours with a preferred extraction time of 2.0 hours. The yield of YMG extracted under the optimum conditions was 30% of bran weight, which also exhibited the highest apparent viscosity (30 mPa.s at 25° C., shear rate 93.32 s$^{-1}$).

Statistical Analysis:

Data were analysed by multiple regressions to fit the following second order (quadratic) polynomial model (Haaland, 1989 and Tong et al., 1984):

$$Y_k = \beta_{ko} + \sum_{i=1}^{4} \beta_{ki} X_i + \sum_{i=1}^{4} \beta_{kii} X_i^2 + \sum_{i=1}^{4} \beta_{kij} X_i X_j$$

where $\beta_{kO}$, $\beta_{ki}$, $\beta_{kii}$ and $\beta_{kij}$ are constant regression coefficients of the model, while $X_i$, $X_j$ are the coded independent variables. The RSREG (Response Surface REGression) program (SAS, 1991) was used for the polynomial regression. The full model fitted polynomial regression equations were expressed graphically (three dimensional and contour plots, respectively) to visualize the relationships between the responses and the independent variables using the Statistical Graphics System procedure of SAS (SAS, 1991).

Equation (1) was fitted to the experimental data (Table 1) to obtain empirical equations for each of the two dependent variables (Table 2). The results of the analysis of variance, goodness-of-fit and the adequacy of the models are summarized in Table 2. The models developed for yield $Y_1$ and apparent viscosity $Y_2$ were adequate with satisfactory $R^2$ values ($R^2$=0.9029 and 0.8101, respectively) and significant F values (probability of F<0.01) (Henika, 1982).

TABLE 2

Regression coefficient and analysis of variance of the second order polynomial[a] for two response variables

| | Response Variables | |
|---|---|---|
| | $Y_1$ (Yield) | $Y_2$ (Apparent viscosity) |
| $\beta_0$ | −0.4230 | −91.0389** |
| Linear | | |
| $\beta_1$ | 0.5637*** | 1.5491*** |
| $\beta_2$ | −3.8566* | 12.2635** |
| $\beta_3$ | 0.1567 | 0.5281 |
| $\beta_4$ | 3.8160 | 7.1062 |
| Quadratic | | |
| $\beta_{11}$ | −0.0022* | −0.0081*** |
| $\beta_{22}$ | 0.5773*** | −0.5559* |
| $\beta_{33}$ | −0.0025 | −0.0040 |
| $\beta_{44}$ | −0.3409 | 0.2728 |
| $\beta_{12}$ | −0.0295*** | −0.0154 |
| $\beta_{13}$ | −0.0015 | −0.0057 |
| $\beta_{14}$ | −0.0022 | −0.0896 |
| $\beta_{23}$ | 0.0252 | 0.0170 |
| $\beta_{24}$ | −0.2281 | −0.6534 |
| $\beta_{34}$ | 0.0179 | 0.0223 |
| Variability explained = | | |
| $R^2$ | 0.9029 | 0.8101 |
| F | 8.637 | 3.962 |
| Probability of F | 0.00 | 0.01 |

[a]Model on which $X_1$ = temperature, $X_2$ = pH, $X_3$ = water:solid ratio and $X_4$ = extraction time is:

$$Y_k = \beta_{ko} + \sum_{i=1}^{4} \beta_{ki} X_i + \sum_{i=1}^{4} \beta_{kii} X_i^2 + \sum_{i=1}^{4} \beta_{kij} X_i X_j$$

***significant at 0.01 level
**significant at 0.05 level
*significant at 0.10 level Steady flow and small strain oscillatory rheological tests were carried out on a Bohlin VOR Rheometer (Bohlin Reologi, Sweden). A concentric cylinder geometry with height of 63.0 mm, radii of the inner and outer containers of 12.5 and 13.75 mm, respectively, was used to probe the rheological behaviour of solutions/dispersions and mixed gels of crude YMG and locust bean gum (LBG, Sigma Chemical Co., USA).

Figure 5A:
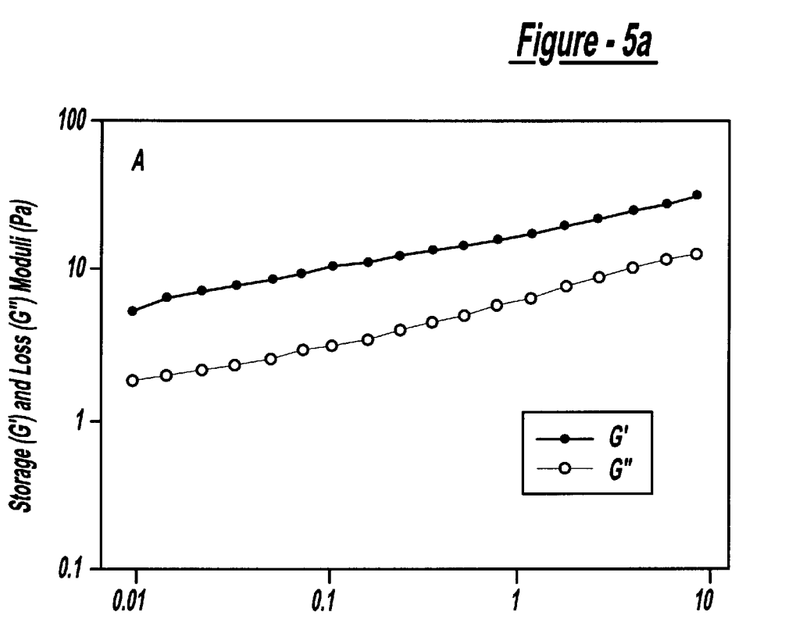
FIG. 5 illustrates in A the Mechanical spectrum of YMG; and in B, the comparison of storage modulus G' of YMG and gums extracted from various conditions (Table 1). Polymer concentration was 2.0% (23° C.).
Figure 5B:
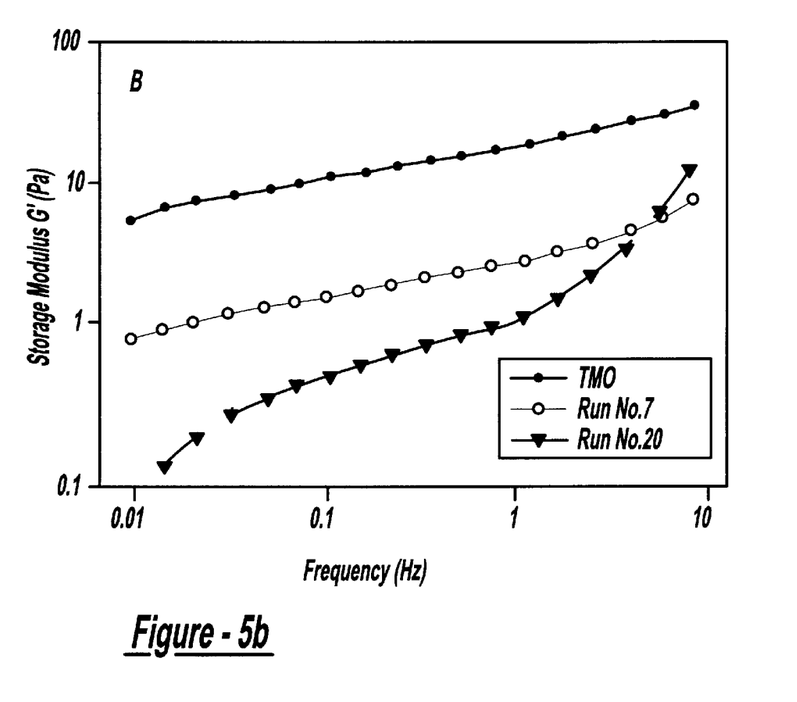

The steady flow rheological property of YMG extracted under the optimum conditions are compared with samples extracted at various conditions. It is clear that YMG exhibited highest apparent viscosity and the curve is characteristic of shear thinning in nature, which is comparable to that of mucilage extracted from whole yellow mustard seeds (Cui et al., 1993a). The ability of YMG to interact with galactomannans to result in synergistic effect illustrated in FIG. 5 where synergistic interactions were observed between YMG and LBG at ratio 9:1, which is again, comparable to the synergistic interactions observed for yellow mustard mucilage extracted from whole seeds (Cui et al., 1995c).

Cosmetic and Skin Care Formulations: A moisturizing lotion was prepared by using the YMG extracted according to the process of the present invention. The details of the ingredients used in this moisturizing lotion are as follows:

| Phase | Ingredient[1] | Percent by Weight |
|---|---|---|
| A1 | De-ionized Water | 73.30% |
| A2 | Cabomer | 0.30% |
| B3 | Triethanolamine | 0.10% |
| B4 | De-ionized Water | 1.00% |
| C5 | Glyceryl Stearate (and) PEG-100 Stearate | 5.00% |
| C6 | Cetyl Alcohol | 2.00% |
| C7 | High Oleic Acid Canola Oil | 2.00% |
| C8 | Dimethicone Copolyol | 1.00% |
| D9 | YMG[2] | 15.00% |
| D10 | Propylene Glycol (and) Diazolidinylurea (and) Methylparaben (and) Propylparaben | 0.30% |

[1] The International Nomenclature for Cosmetic Ingredient (INCI) names were used in the ingredient listing.
[2] The YMG used was a solution of 1.5% pre-made solution.

The ingredients in Phase A were combined and heated to 78° C. The ingredients in Phase B were combined and added into Phase A at 78° C. In a separate container, all the ingredients in Phase C were combined and heated to 78° C. Phase C was poured into Phase AB. The mixed Phase ABC was cooled to about 45° C. and Phase D was added in one at a time.

Figure 6:
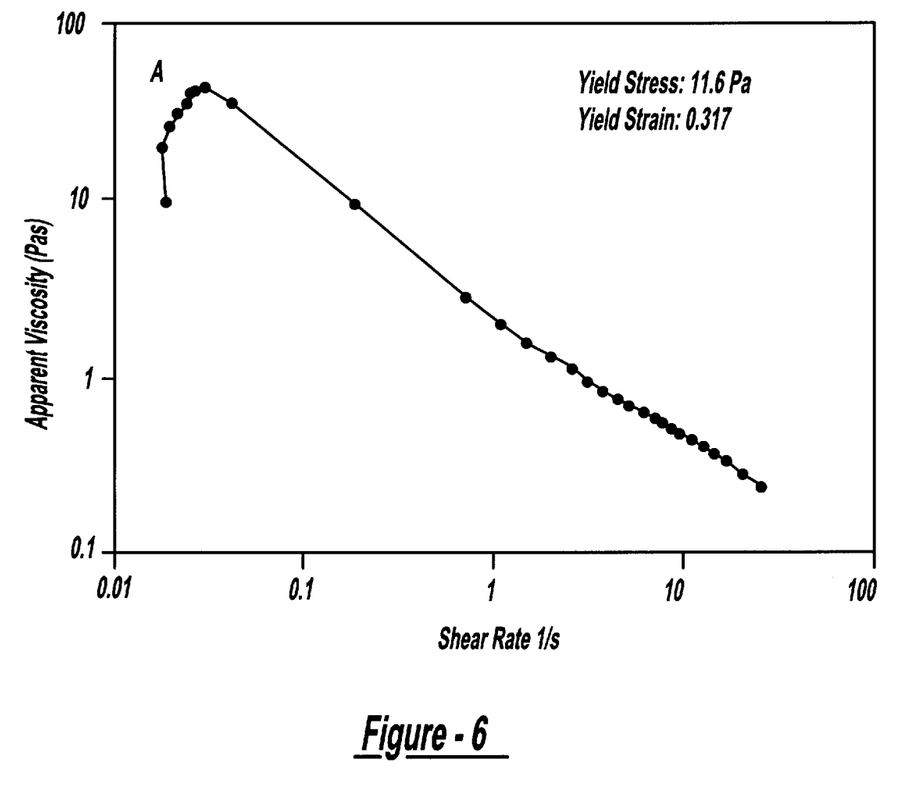
FIG. 6 illustrates the flow behaviour of the prepared moisturizing lotion at 25° C.
Figure 7:
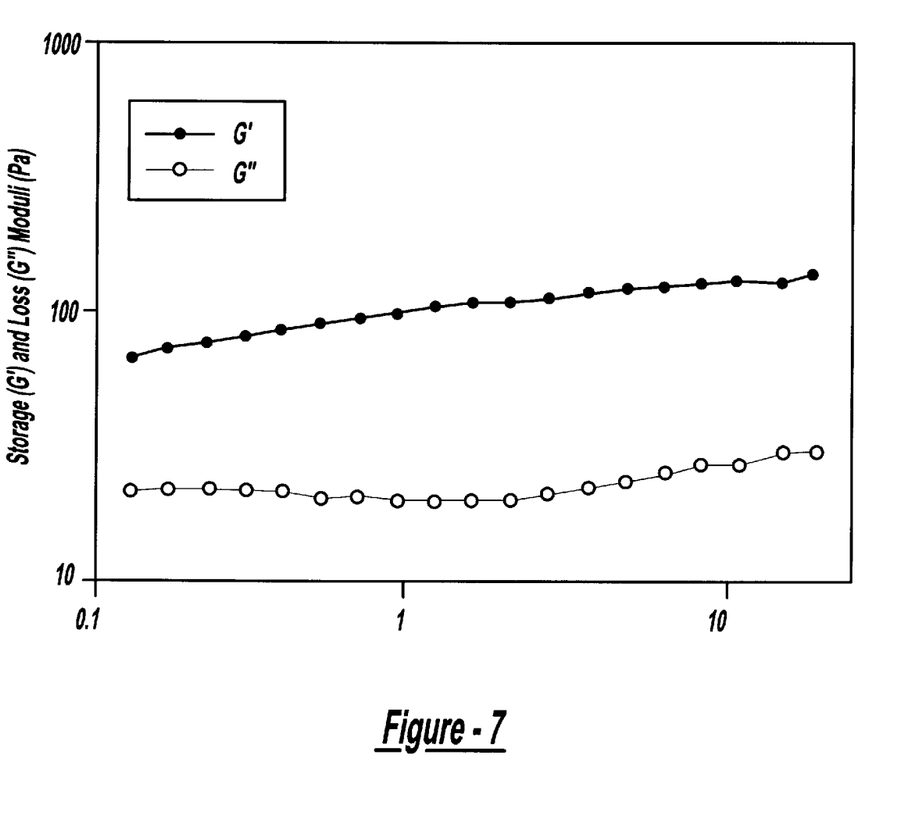
FIG. 7 illustrates the dynamic rheological properties of the prepared moisturizing lotion at 25° C.
Figure 8:
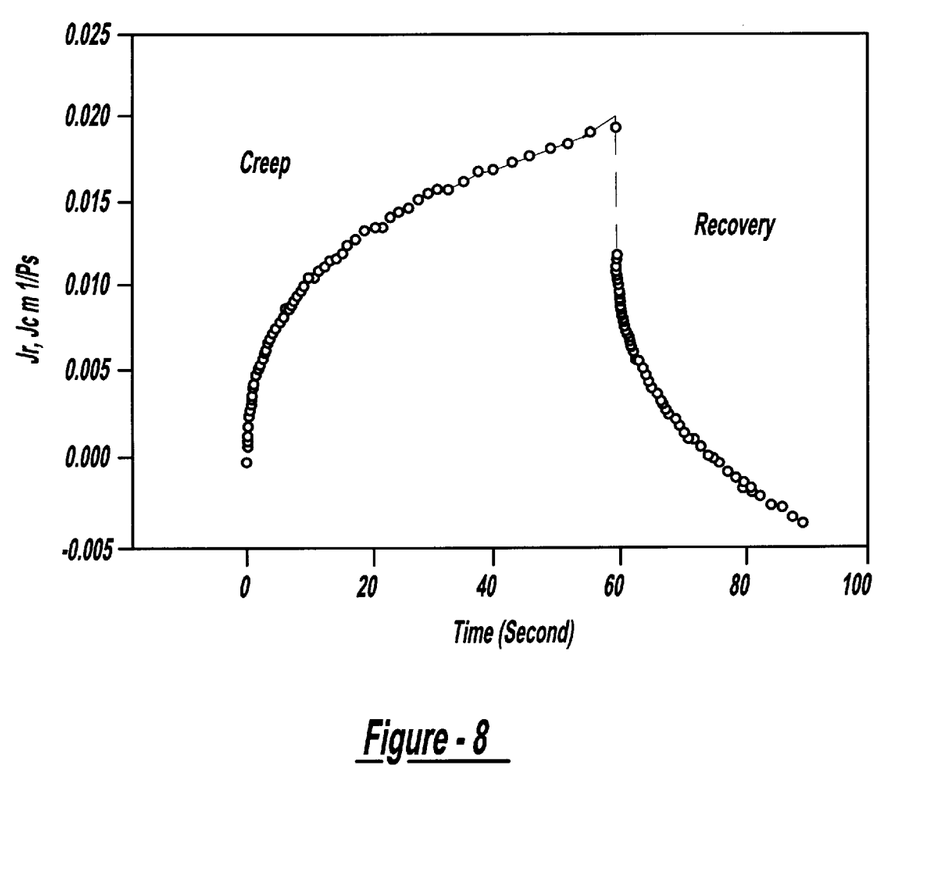
FIG. 8 illustrates the creep-recovery test of the prepared moisturizing lotion at 25° C.

The prepared moisturizing lotion has a yield stress of 11.6 Pa and a shear thinning property as its viscosity decreases with the increase of shear rate (FIG. 6). This lotion also has a gel structure as evaluated by oscillation rheological test; the storage modulus G' is much greater than the loss modulus G" and file two parameters are independent of frequency (FIG. 7). This strong structure is also shown in the creep-recovery test in which there is a sharp recovery structure at the moment the creep stress is stopped. The complete recovery was achieved within 20 seconds (FIG. 8)

The above-described embodiments of the present invention are meant to be illustrative of preferred embodiments of the present invention and are not intended to limit the scope of the present invention. Various modifications, which would be readily apparent to one skilled in the art, are intended to be within the scope of the present invention. The only limitations to the scope of the present invention are set out in the following appended claims.

Prior Art References:

Cui, W., Eskin, N. A. M. and Biliaderis, C. G. (1993a). Chemical and physical properties of yellow mustard (*Sinapis alba L.*) mucilage. Food Chem., 46, 169–176.

Cui, W., Eskin, N. A. M. and Biliaderis, C. G. (1993b). Water-soluble yellow mustard (*Sinapis alba L.*) polysaccharides: partial characterization, molecular size distribution and rheological properties. Carbohydr. Polym., 20, 215–225.

Cui, W., Eskin, N. A. M. and Biliaderis, C. G. (1994a). Fractionation, structural analysis and rheological properties of water-soluble yellow mustard (*Sinapis alba L.*) polysaccharides. J. Agric. Food Chem. 42, 657–664.

Cui, W., Eskin, N. A. M. and Biliaderis, C. G. (1994b). Yellow mustard mucilage: chemical structure and rheological properties. Food Hydrocoll., 8, 204–213.

Cui, W., Mazza, G., Oomah, B. D. and Biliaderis, C. G. (1994c). Optimization of an aqueous extraction process of flaxseed gum by response surface methodology. Lebenms. Wiss. u.-Technol. 8, 363–369.

Cui, W., Eskin, N. A. M. and Biliaderis. (1995a). NMR characterization of a 1,4-linked β-D-glucan having ether groups from yellow mustard (*Sinapis alba L.*) mucilage. Carbohydr. Polym., 27, 117–122.

Cui, W., Eskin, N. A. M., Biliaderis, C. G. and Mazza, G. (1995b). Synergistic interactions between yellow mustard polysaccharides and galactomannans. Carbohydr. Polym., 27, 123–127.

Cui, W., Eskin, N. A. M., Biliaderis, C. G. and Marat, K. (1995c). NMR characterization of a 4-O-Methyl-β-D-glucuronic acid containing rhamnogalacturonan from yellow mustard (*Sinapis alba L.*) mucilage. Carbohydr. Res., in press.

Gacula, M. C. and Singh, J. (1984). Statistical methods in food and consumer research. Academic Press. pp. 241.

Giovanni, M. (1983) Response surface methodology and product optimization. Food Technol., 11, 41–45.

Haaland, P. D. (1989). Experimental design in biotechnology. Marcel Dekker, Inc. New York and Basel. pp. 243.

Henika, R. G. (1982). Use of response surface methodology in sensory evaluation. Food Technol. 36(11), 96–101.

SAS Institute, Inc.(1991). SAS/STAT User's Guide, Version 6, 4th ed., SAS Institute Cary, N.C.

Sharafabadi, S. K.; U.S. Pat. No. 4,980,186.

Siddiqui, I. R., Yiu, J. D., Jones, J. D. and Kalab, M. (1986). Mucilage in yellow mustard (Brassica hirta) seeds. Food Microstruct., 5, 157–162.

Tong, P. S., Jordan, W. K. and Houghton, G. (1984). Response surface methodology to study fat destabilization and development of overrun in ice cream produced with polyunsaturated safflower oil and milk fat blends. J. Dairy Sci., 67, 779–793.

Embodiments in which exclusive property or privilege is claimed are as follows:

1. A process for extracting the gum from yellow mustard bran, comprising a first step of treating the yellow mustard bran with water to form a water:solid solution, a second step of separating the resulting water extract from the seed bran, and a third step of separating the yellow mustard gum from the water wherein, wherein:

a) in the first step, the water is heated to a temperature in the range of about 50–70° C.;

b) in the first step, the water:solid ratio is in the range of about 40:1–60:1;

c) in the second step, the pH of the water:solid solution is in the range of about 7.0–10.0; and d) the extraction time from the first through the third step is in the range of about 2 to 2.5 hours.

2. The process of claim 1 wherein the water temperature is about 55° C.

3. The process of claim 1 wherein the pH is in the range of about 8.0–9.5.

4. The process of claim 1 wherein the water:solid ratio is about 50:1.

5. The process of claim 1 wherein said extraction time is about 2.0 hours.

6. A yellow mustard gum produced from the process as claimed in claim 1.

7. A composition for application to skin comprising the yellow mustard gum of claim 6.

* * * * *